United States Patent

Nakagawa et al.

[11] Patent Number: 5,401,431
[45] Date of Patent: Mar. 28, 1995

[54] CLEANING-PRESERVING AQUEOUS SOLUTION FOR CONTACT LENSES AND METHOD FOR CLEANING AND DISINFECTING A CONTACT LENS BY MEANS THEREOF

[75] Inventors: Akira Nakagawa; Kisaki Maezawa, both of Nagoya, Japan

[73] Assignee: Tomei Sangyo Kabushiki Kaisha, Nagoya, Japan

[21] Appl. No.: 128,111

[22] Filed: Sep. 29, 1993

[30] Foreign Application Priority Data

Oct. 1, 1992 [JP] Japan .................. 4-286856

[51] Int. Cl.$^6$ .............. C11D 1/72; B08B 7/00
[52] U.S. Cl. ................. 252/174.21; 252/106; 252/173; 134/40; 134/42
[58] Field of Search ............. 252/106, 174.21, 173; 134/40, 42

[56] References Cited

U.S. PATENT DOCUMENTS

| | | | |
|---|---|---|---|
| 4,029,817 | 6/1977 | Blanco et al. | 424/329 |
| 4,614,549 | 9/1986 | Ogunbiyi et al. | 134/19 |
| 4,748,189 | 5/1988 | Su et al. | 514/781 |
| 4,900,366 | 2/1990 | Sibley et al. | 134/42 |

FOREIGN PATENT DOCUMENTS

| | | |
|---|---|---|
| 0079030 | 5/1983 | European Pat. Off. . |
| 3526125 | 1/1987 | Germany . |
| 2115116 | 4/1990 | Japan . |
| 3068503 | 3/1991 | Japan . |
| 4164002 | 6/1992 | Japan . |
| 4342508 | 11/1992 | Japan . |
| 5170643 | 7/1993 | Japan . |
| WO85/01209 | 3/1985 | WIPO . |

*Primary Examiner*—Paul Lieberman
*Assistant Examiner*—Lorna M. Douyon
*Attorney, Agent, or Firm*—Oblon, Spivak, McClelland, Maier & Neustadt

[57] ABSTRACT

A cleaning-preserving aqueous solution for contact lenses, which contains, as a surfactant, a tetra-fatty acid polyoxyethylene sorbitol of the formula 1:

$$\begin{array}{l} CH_2O(CH_2CH_2O)_aR_1 \\ | \\ CHO(CH_2CH_2O)_bR_2 \\ | \\ CHO(CH_2CH_2O)_cR_3 \\ | \\ CHO(CH_2CH_2O)_dR_4 \\ | \\ CHO(CH_2CH_2O)_eR_5 \\ | \\ CH_2O(CH_2CH_2O)_fR_6 \end{array}$$

wherein $a+b+c+d+e+f=20$ to $50$, and four among $R_1$ to $R_6$ are $C_{12-18}$ saturated or unsaturated fatty acid residues and the remaining two are hydrogen atoms, and which has a physiological osmotic pressure and has a pH adjusted to a level of from 4 to 9.

9 Claims, No Drawings

CLEANING-PRESERVING AQUEOUS SOLUTION FOR CONTACT LENSES AND METHOD FOR CLEANING AND DISINFECTING A CONTACT LENS BY MEANS THEREOF

The present invention relates to a cleaning-preserving aqueous solution for contact lenses and a method for cleaning and disinfecting a contact lens by means of such a solution. More particularly, it relates to a composition of a cleaning-preserving aqueous solution for contact lenses which is useful for both hydrophobic contact lenses and hydrophilic contact lenses and an effective method for cleaning and disinfecting a contact lens by means of such a cleaning-preserving aqueous solution.

Contact lenses are generally classified into hydrophilic contact lenses and hydrophobic contact lenses. Irrespective of their types, soils such as proteins, lipids or inorganic substances derived from tears or sebum will deposit on such contact lenses. Therefore, it is necessary to clean them periodically. Further, in the case of hydrophilic contact lenses, bacteria, etc. are likely to deposit thereon, and it is necessary to conduct disinfection by means of a method such as heat disinfection or chemical disinfection.

To remove lipid soil deposited on a contact lens, it is common that after removing the contact lens from the eye every day, the contact lens is subjected to cleaning treatment such as soaking or rubbing with fingers by means of a cleaning solution containing a surfactant. When cleaning is conducted by means of a cleaning solution containing a surfactant, there will be no particular problem in the case of a hydrophobic contact lens, but in the case of a hydrophilic contact lens, the surfactant is likely to be adsorbed in the interior of the contact lens, whereby a problem of adversely affecting the contact lens tends to result such that if heat disinfection such as boiling is conducted after the cleaning, the contact lens tends to be turbid or swelled.

Accordingly, when a hydrophilic contact lens was washed with a cleaning solution containing a surfactant, it used to be necessary to thoroughly rinse the contact lens with e.g. a preserving solution containing no surfactant and to remove the surfactant completely before the contact lens could be subjected to heat disinfection. Therefore, the user had to carry the cleaning solution and the preserving solution, and had to conduct cleaning and disinfection of the contact lens by cumbersome operations. Further, if heat disinfection was conducted by a cleaning solution by mistake, the contact lens would no longer be useful.

Under such circumstances, it has been proposed to employ, as a surfactant to be incorporated to a cleaning solution for contact lenses, a polymer surfactant which is generally considered to be hardly adsorbed on a hydrophilic contact lens. Japanese Unexamined Patent Publications No. 124009/1977 and No. 121416/1985 disclose specific examples of surfactants which can be heated. However, surfactants so far proposed, had a problem that they could not be commonly used, since adsorption was likely to result depending upon the materials of the contact lenses, and thus they were likely to give adverse effects such as turbidity and swelling to the contact lenses.

The present invention has been made under these circumstances, and it is an object of the present invention to provide a cleaning solution containing a surfactant, which can be commonly used for various contact lens materials, which is highly safe without adversely affecting contact lenses even when used for disinfection by boiling and which, nevertheless, provides high cleaning effects. Further, it is another object of the present invention to provide an effective method for cleaning and disinfecting a contact lens by means of such a cleaning solution.

As a result of an extensive research to accomplish the above objects, the present inventors have found that among various surfactants, tetra-fatty acid polyoxyethylene sorbitols are capable of satisfying the above-mentioned various conditions. The present invention has been accomplished on the basis of such a discovery.

Thus, the present invention provides a cleaning-preserving aqueous solution for contact lenses, which contains, as a surfactant, a tetra-fatty acid polyoxyethylene sorbitol of the formula 1:

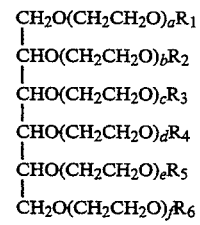

wherein $a+b+c+d+e+f=20$ to 50, and four among $R_1$ to $R_6$ are $C_{12\text{-}18}$ saturated or unsaturated fatty acid residues and the remaining two are hydrogen atoms, and which has a physiological osmotic pressure and has a pH adjusted to a level of from 4 to 9.

The present invention also provides a method for cleaning a contact lens, which comprises soaking the contact lens in the cleaning-preserving aqueous solution for contact lenses, to remove a soil deposited on the contact lens.

Further, the present invention provides a method for cleaning and disinfecting a contact lens, which comprises soaking the contact lens in the cleaning-preserving aqueous solution for contact lenses, and heating the solution to a temperature of from 80° to 100° C., to remove a soil deposited on the contact lens and to disinfect the contact lens.

In short, the cleaning-preserving aqueous solution of the present invention contains, as a surfactant, a tetra-fatty acid polyoxyethylene sorbitol which simultaneously has characteristics such that it is scarcely adsorbed by various hydrophobic and hydrophilic contact lens materials, and it is highly safe and has high cleaning effects. Accordingly, the washing-preserving solution has an extremely wide common usage, such that it can be used for cleaning various contact lenses irrespective of hydrophobic or hydrophilic contact lenses, to conduct safe and effective cleaning. Further, with such a cleaning-preserving aqueous solution, no adsorption of the surfactant will result even to a hydrophilic contact lens, whereby it is possible to conduct disinfection by boiling at the same time as cleaning the contact lens, in the cleaning-preserving aqueous solution. Accordingly, cleaning and disinfection treatments of hydrophilic contact lenses can thereby be conducted very simply, and a problem such as turbidity or swelling of a contact lens by misuse of a treating solution can thereby be eliminated.

Cleaning treatment of a contact lens can be conducted very simply by soaking the contact lens in such a cleaning-preserving aqueous solution. Likewise, cleaning and disinfection treatment can be conducted very simply by soaking the contact lens in such a cleaning-preserving aqueous solution and heating the solution.

Now, the present invention will be described in detail with reference to the preferred embodiments.

The tetra-fatty acid polyoxyethylene sorbitol to be incorporated as a surfactant to the cleaning-preserving aqueous solution for contact lenses according to the present invention, is of the type having a structure of the above-mentioned formula 1 wherein four among $R_1$ to $R_6$ are $C_{12-18}$ saturated or unsaturated fatty acid residues (RCO— wherein R is a saturated or unsaturated fatty acid group), and the remaining two among $R_1$ to $R_6$ are hydrogen atoms, and it has characteristics such that it is highly safe and has high cleaning effects. In the present invention, among such sorbitols, the one wherein the average number of mols of polyoxyethylenes added (a+b+c+d+e+f) is from 20 to 50, preferably from about 30 to about 40. If the average number of mols of polyoxyethylenes added is less than 20, the solubility tends to be substantially low, while if it exceeds 50, adsorption to the lens is likely to result, whereby in a case of a hydrophilic contact lens, an adverse effect such as turbidity or swelling is likely to result.

Specific examples of such a tetra-fatty acid polyoxyethylene sorbitol include tetraoleic acid polyoxyethylene (30) sorbitol, tetraoleic acid polyoxyethylene (40) sorbitol, tetrastearic acid polyoxyethylene (40) sorbitol and tetralauric acid polyoxyethylene (20) sorbitol. These surfactants are commercially available as "Leodol 430", "Leodol 440" (manufactured by Kao Corporation), "GO-430" and "GO-440" (manufactured by Nikko Chemical Co., Ltd.). Such a surfactant is added usually in an amount of from 0.0005 to 1% by weight, preferably from 0.001 to 0.1% by weight. If the amount of the surfactant is too small, the cleaning force will be inadequate. On the other hand, if it is too much, no further increase in the cleaning force can be expected.

With the cleaning-preserving aqueous solution for contact lenses according to the present invention, the pH must be within a physiologically acceptable range and is adjusted usually within a range of pH 4 to 9, preferably pH 6 to 8. For this purpose, a buffering agent may be incorporated to the cleaning-preserving aqueous solution, as the case requires. There is no particular restriction to such a buffering agent, and various conventional buffering agents of e.g. boric acid type, citric acid type or phosphoric acid type may be employed.

Further, when such a cleaning-preserving aqueous solution for contact lenses is to be used for hydrophilic contact lenses, the osmotic pressure is required to be adjusted to be a physiological osmotic pressure. If the osmotic pressure is not within the physiological range, irritation to the eye is likely to result. Specifically, the osmotic pressure is adjusted to be within a range of from about 200 to about 800 mOsm/kg water. For this purpose, a tonicity-controlling agent such as sodium chloride, potassium or glycerol, or the above-mentioned buffering agent may be added to the cleaning-preserving aqueous solution, as the case requires.

Further, preservatives, bacteriocides, viscosity builders, metal chelating agents, protein removing agents such as enzymes or oxidizing agents, etc. may be added to the cleaning-preserving aqueous solution for contact lenses according to the present invention, as the case requires.

Among them, preservatives and bacteriocides are added to prevent propagation of fungi or bacteria during the storage or for the purpose of disinfection. For example, sorbic acid, benzoic acid or salts thereof, p-oxybenzoates, quaternary ammonium salts or hydrogen peroxide may optionally be employed. Viscosity builders are added to facilitate cleaning when contact lenses are cleaned by rubbing with fingers, and carboxymethylcellulose and polyvinyl alcohol may, for example, be optionally selected for use. Further, metal chelating agents are added to remove soils of inorganic salts derived from e.g. tears or to prevent deposition of such soils to contact lenses. Ethylenediamine tetraacetic acid, nitrilotriacetic acid or a salt thereof may, for example, be used. Protein-removing agents are added to remove protein soils derived from e.g. tears or to prevent deposition of such soils to contact lenses. An enzyme such as protease or amylase, or an oxidizing agent such as hypochlorous acid may be employed.

The cleaning-preserving aqueous solution for contact lenses thus prepared, contains the above-mentioned tetra-fatty acid polyoxyethylene sorbitol as a surfactant, whereby safe and effective cleaning can be conducted without giving no adverse effect not only to hydrophobic lens materials but also to hydrophilic lens materials, and it has a wide range of common usage. Hydrophilic contact lenses usually have a water content of from about 30% to about 80%, and they are classified into those made of ionic materials and those made of nonionic materials. The cleaning-preserving aqueous solution for contact lenses of the present invention can be used for contact lenses made of either materials. Specifically, hydrophilic contact lenses are made of polymers or copolymers composed essentially of one or more monomers such as 2-hydroxyethyl methacrylate, methyl methacrylate, triethylene glycol methacrylate, dimethylacrylamide, N-vinylpyrrolidone, polyvinyl alcohol and methacrylic acid.

To clean a contact lens by means of such a cleaning-preserving aqueous solution for contact lenses, a usual soaking method or a rubbing method is employed. Among them, a method of soaking the contact lens in the cleaning-preserving aqueous solution, is advantageously selected. With respect to the temperature condition at the time of soaking, the operation may be conducted at a room temperature or under heating to a temperature of not higher than 100° C. The soaking time may be from 5 minutes to 24 hours, and the cleaning power increases under heating.

In the case of a hydrophilic contact lens, disinfection is required in addition to cleaning of the lens. Therefore, a method is advantageously selected which comprises soaking the contact lens in the above-mentioned cleaning-preserving aqueous solution and heating the cleaning-preserving aqueous solution to a temperature of from 80° to 100° C., whereby not only cleaning but disinfection under heating can be conducted, and treatment of the hydrophilic contact lens can be conducted very simply. The disinfection can adequately be conducted usually by heating for a period within 60 minutes. Further, such an operation is free from bringing about an adverse effect to the lens such as turbidity or swelling of the lens. After the disinfection, the contact lens may be stored in the solution in the same manner as usual, or the contact lens may be taken out from the solution and put on the eye as it is.

Now, the present invention will be described in further detail with reference to some Examples for the cleaning-preserving aqueous solution for contact lenses and the method for cleaning and disinfection according to the present invention. However, it should be understood that the present invention is by no means restricted by such specific Examples. Further, it should be understood that various changes, modifications or improvements may be made on the basis of the common knowledge of those skilled in the art without departing from the spirit of the present invention, in addition to the following Examples and the specific embodiments described above.

EXAMPLE 1

Preparation of Cleaning-preserving Aqueous Solutions

Firstly, three types of cleaning-preserving aqueous solutions were prepared as follows.

(A) 0.40 g of boric acid, 0.031 g of borax, 0.67 g of sodium chloride and 0.1 g of tetraoleic acid polyoxyethylene (40) sorbitol were dissolved in purified water, and the solution was adjusted with water to a volume of 100 ml to obtain a cleaning-preserving aqueous solution A for contact lenses. This solution had pH 7.35 and an osmotic pressure of 286 mOsm/kg.

(B) 0.02 g of citric acid monohydrate, 0.48 g of trisodium citrate dihydrate, 2.0 g of glycerol and 0.05 g of tetraoleic acid polyoxyethylene (30) sorbitol were dissolved in purified water, and the solution was adjusted with water to a volume of 100 ml to obtain a cleaning-preserving aqueous solution B for contact lenses. This solution had pH 6.63 and an osmotic pressure of 281 mOsm/kg.

(C) 0.40 g of boric acid, 0.031 g of borax, 0.66 g of sodium chloride, 0.15 g of potassium sorbate, 0.05 g of disodium ethylenediamine tetraacetate dihydrate and 0.02 g of tetraoleic acid polyoxyethylene (30) sorbitol were dissolved in purified water, and the solution was adjusted with water to a volume of 100 ml to obtain a cleaning-preserving aqueous solution C for contact lenses. This solution had pH 6.81 and an osmotic pressure of 298 mOsm/kg.

Preparation of Artificially Soiled Lenses

On the other hand, 6 g of sorbitan monooleic acid ester, 16 g of castor oil, 35 g of lanolin, 5 g of oleic acid, 4 g of sorbitan trioleic acid ester, 2 g of ethyl alcohol, 2 g of cholesterol and 30 g of cholesterol acetate were mixed and heated to be uniform. Then, 1 g of the mixture was dissolved in a solvent mixture of ethanol/hexane (1/1), and the solution was adjusted with the same solvent mixture to a volume of 100 ml to obtain an artificial tear. Then, 3 $\mu$l of this artificial tear was spread on the outer surface of a dried hydrophilic contact lens (Menicon Soft MA, manufactured by Menicon Co., Ltd.) and dried. Then, the contact lens was soaked in physiological saline to obtain an artificially soiled lens. This lens was inspected by a dark-field microscope, whereby it was observed that lipid-like soil was deposited over the entire surface of the lens.

Cleaning and Disinfection Test

The above-mentioned artificially soiled lenses were soaked in the above cleaning-preserving solutions A to C filled in the lens cases, respectively. Then, the contact lenses in the respective cleaning-preserving aqueous solutions were heated by means of a boiling disinfecting device (Riser Mini, manufactured by Menicon Co., Ltd.). Then, the contact lenses were taken out and inspected by a dark-field microscope, whereby it was observed that the soils were removed, and the lenses were clean.

COMPARATIVE EXAMPLE 1

The artificially soiled lens prepared in Example 1 was soaked in a commercially available preserving solution for contact lenses (Clean Bottle Soak, manufactured by Menicon Co., Ltd.) filled in a lens case. Then, the contact lens in the preserving solution was heated by means of the same boiling disinfecting device as used in Example 1. Then, the contact lens was taken out and inspected by a dark-field microscope, whereby it was observed that the soil remained without being removed substantially.

EXAMPLE 2

Firstly, an artificially soiled lens was prepared in the same manner as in the preparation of artificially soiled lenses in Example 1 using a hydrophobic contact lens (Menicon EX, manufactured by Menicon Co., Ltd.), and it was confirmed under a dark-field microscope that the soil was deposited over the entire surface of the lens. Then, a few drops of the cleaning-preserving aqueous solution A prepared in Example 1 were dropped on the artificially soiled lens, and the lens was rubbed with fingers for cleaning and rinsed with tap water. Then, it was inspected again by a dark-field microscope, whereby it was observed that the soil was removed, and the lens was clean.

EXAMPLE 3

A hydrophilic contact lens having a base curve of 8.40 mm, a degree of −4.00 D and a diameter of 13.0 mm (Menicon Soft MA, manufactured by Menicon Co., Ltd.) was soaked in the washing-preserving aqueous solution C prepared in Example 1, filled in a lens case. Then, the contact lens in the cleaning-preserving aqueous solution was heated by means of the same boiling disinfecting device as used in Example 1. Then, it was left to cool and stored for from 6 to 8 hours. This operation was regarded as one cycle and repeated for 30 cycles, whereupon the base curve, the degree and the diameter of the contact lens were examined, and the change of the outer appearance was inspected by a dark-field microscope, whereby no adverse effect to the contact lens was observed.

COMPARATIVE EXAMPLE 2

With respect to the cleaning-preserving aqueous solution C prepared in Example 1, the surfactant was changed to 0.02 g of a polyoxypropylene-polyoxyethylene adduct of ethylenediamine (Synperonic T/908, manufactured by ICI), to obtain a cleaning-preserving aqueous solution D. Using this cleaning-preserving aqueous solution D, the same cycle test as in Example 3 was conducted, whereby the contact lens became turbid and useless.

COMPARATIVE EXAMPLE 3

With respect to the cleaning-preserving aqueous solution C prepared in Example 1, the surfactant was changed to 0.02 g of tetraoleic acid polyoxyethylene (60) sorbitol, to obtain a cleaning-preserving aqueous solution E. Using this cleaning-preserving aqueous solution E, the same cycle test as in Example 3 was conducted, whereby the contact lens became turbid and useless.

EXAMPLE 4

A swelled contact lens material composed mainly of poly-2-hydroxyethyl methacrylate and having a water content of 38% (diameter: 1.8 cm) was prepared, and this material was cut into a thickness of 1 mm and then further divided into four pieces to obtain chips. 4 g of the chips were put into a vial, and 10 ml of the cleaning-preserving solution A prepared in Example 1 was added thereto and boiled for 20 minutes, and left to cool for one hour. Then, the surfactant in the cleaning-preserving aqueous solution was quantified, and the obtained value was compared with the value preliminarily quantified prior to the boiling to examine adsorption of the surfactant to the contact lens material. The quantitative analysis of the surfactant in the cleaning-preserving aqueous solution was conducted in accordance with a cobalt thiocyanate method ("New Surfactant Analysis", compiled by Surfactant Analysis Research Society, Yuki Shobo, 1987, p. 324). As a result, no change was observed in the content of the surfactant in the cleaning-preserving aqueous solution, and thus it was found that the surfactant was not adsorbed to the contact lens material even when the cleaning-preserving aqueous solution was boiled.

EXAMPLE 5

A swelled contact lens material made of a copolymer composed essentially of dimethylacrylamide and having a water content of 72% (diameter: 1.8 cm) was prepared, and this material was cut into a thickness of 1 mm and further divided into four pieces to obtain chips. Then, 4 g of the chips were put into a glass vial, and 10 ml of the cleaning-preserving aqueous solution B prepared in Example 1, was added thereto, boiled for 20 minutes and left to cool for one hour. Then, in the same manner as in Example 4, the surfactant in the washing-preserving aqueous solution was quantified, and the value obtained was compared with the value preliminarily quantified prior to the boiling to examine adsorption of the surfactant to the contact lens material. As a result, no change was observed in the content of the surfactant in the washing-preserving aqueous solution, and it was found that the surfactant was not adsorbed to the contact lens material even when the cleaning-preserving aqueous solution was boiled.

COMPARATIVE EXAMPLE 4

With respect to the cleaning-preserving aqueous solution A prepared in Example 1, the surfactant was changed to 0.1 g of polyoxyethylene (70) nonylphenyl ether, to obtain a cleaning-preserving aqueous solution F. Using this cleaning-preserving aqueous solution F, the same test as in Example 4 was conducted, except that for the quantitative analysis of the surfactant, absorption at 274 nm was measured, and the amount of the surfactant was obtained from a calibration curve preliminarily prepared. As a result, the concentration of the solution surrounding the lens chips after boiling was reduced to 0.04%, from which the liquid concentration within the lens chips was determined to be 0.434%. Thus, the surfactant was taken into the lens chips in an amount as much as 11.2 times of the concentration of the solution surrounding the lens chips.

We claim:

1. A cleaning-preserving aqueous solution suitable for cleaning and preserving contact lenses, which contains, as a surfactant, a tetra-fatty acid polyoxyethylene sorbitol of the formula 1:

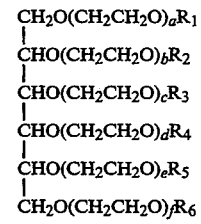

wherein $a+b+c+d+e+f=20$ to 50, and four among $R_1$ to $R_6$ are $C_{12-18}$ saturated or unsaturated fatty acid residues and the remaining two are hydrogen atoms, said solution having a physiological osmotic pressure and a pH adjusted to a level of from 4 to 9.

2. The cleaning-preserving aqueous solution for contact lenses according to claim 1, wherein in the formula 1, $a+b+c+d+e+f=$ about 30 to about 40.

3. The cleaning-preserving aqueous solution for contact lenses according to claim 1, wherein the sorbitol is selected from the group consisting of tetraoleic acid polyoxyethylene (30) sorbitol, tetraoleic acid polyoxyethylene (40) sorbitol, tetrastearic acid polyoxyethylene (40) sorbitol and tetralauric acid polyoxyethylene (20) sorbitol.

4. The cleaning-preserving aqueous solution for contact lenses according to claim 1, wherein the sorbitol is in an amount of from 0.0005 to 1% by weight.

5. The cleaning-preserving aqueous solution for contact lenses according to claim 1, wherein the sorbitol is in an amount of from 0.001 to 0.1% by weight.

6. The cleaning-preserving aqueous solution for contact lenses according to claim 1, which has a pH adjusted to a level of from 6 to 8.

7. The cleaning-preserving aqueous solution for contact lenses according to claim 1, wherein the physiological osmotic pressure is from about 200 to about 800 mOsm/kg.

8. A method for cleaning a contact lens, which comprises soaking the contact lens in the cleaning-preserving aqueous solution for contact lenses as defined in claim 1, to remove a soil deposited on the contact lens.

9. A method for cleaning and disinfecting a contact lens, which comprises soaking the contact lens in the cleaning-preserving aqueous solution for contact lenses as defined in claim 1, and heating the solution to a temperature of from 80° to 100° C., to remove a soil deposited on the contact lens and to disinfect the contact lens.

* * * * *